United States Patent [19]
Kraus

[11] Patent Number: 6,050,969
[45] Date of Patent: Apr. 18, 2000

[54] PRESSURE INDICATOR

[75] Inventor: Robert G. Kraus, Attleboro, Mass.

[73] Assignee: Johnson & Johnson Professional, Inc., Raynham, Mass.

[21] Appl. No.: 09/062,334

[22] Filed: Apr. 17, 1998

[51] Int. Cl.[7] .................................................. A61M 5/00
[52] U.S. Cl. ................................................. 604/9; 600/12
[58] Field of Search .............................. 604/8, 9; 600/12, 600/15; 33/355 R, 364, 355 D, 370, 371, 372

[56] References Cited

U.S. PATENT DOCUMENTS

| | | | |
|---|---|---|---|
| 3,423,672 | 1/1969 | Stockton . | |
| 4,146,029 | 3/1979 | Ellinwood, Jr. | 128/260 |
| 4,204,547 | 5/1980 | Allocca | 128/748 |
| 4,360,007 | 11/1982 | Levy et al. | 128/899 |
| 4,438,568 | 3/1984 | Kramer et al. | 33/348 |
| 4,443,214 | 4/1984 | Marion | 604/9 |
| 4,540,400 | 9/1985 | Hooven | 604/9 |
| 4,551,128 | 11/1985 | Hakim et al. | 604/9 |
| 4,595,390 | 6/1986 | Hakim et al. | 604/9 |
| 4,608,992 | 9/1986 | Hakim et al. | 128/654 |
| 4,615,691 | 10/1986 | Hakim et al. | 604/9 |
| 4,676,772 | 6/1987 | Hooven | 604/9 |
| 4,700,490 | 10/1987 | Kramer et al. | 33/355 D |
| 4,772,257 | 9/1988 | Hakim et al. | 604/9 |
| 5,146,687 | 9/1992 | Kjellstrom | 33/355 R |
| 5,187,871 | 2/1993 | McDermott | 33/354 |
| 5,637,083 | 6/1997 | Bertrand et al. | 604/9 |
| 5,643,194 | 7/1997 | Negre | 604/8 |

OTHER PUBLICATIONS

Article Entitled, "The SOPHY Programmable Pressure Valve Model SU8," appears to correspond to U.S. Patent No. 4,443,214. Horological Technology to benefit the Neurosurgeon.

Advertisement material for Medtronic, STRATA™ Adjustable Delta Valve.

*Primary Examiner*—Ronald Stright
*Assistant Examiner*—Jeremy Thissell
*Attorney, Agent, or Firm*—Nutter, McClennen & Fish, LLP

[57] ABSTRACT

A shunt valve system includes an implantable shunt valve and a device for obtaining pressure setting information from the shunt valve after it is implanted under the scalp of a patient. The device includes a housing that is externally mountable on the patient's head proximate the shunt valve. A fluid-filled chamber is formed in the housing in which a ferromagnetic indicator is movable. The position of the ferromagnetic indicator corresponds to an indicator magnet located within the implanted shunt valve. In one embodiment, the indicator magnet is affixed to a cam which forms a portion of a stepping motor used to a select a pressure setting for the shunt valve. From the position of the ferromagnetic indicator, which corresponds to the indicator magnet and the cam, the pressure setting of the shunt valve can be determined.

13 Claims, 5 Drawing Sheets

PRESSURE INDICATOR

CROSS REFERENCE TO RELATED APPLICATION

Not Applicable.

STATEMENT REGARDING FEDERALLY SPONSORED RESEARCH

Not Applicable.

FIELD OF THE INVENTION

The present invention relates to devices for obtaining information from an apparatus and more particularly to a system including an implantable apparatus and a device for obtaining pressure setting information of the apparatus after implantation.

BACKGROUND OF THE INVENTION

Many types of medical apparatus are implanted at various locations in the body on a permanent or semi-permanent basis. However, after implantation it is often difficult to obtain information from the implanted apparatus. One such type of implantable apparatus is a shunt valve and catheter used in the treatment of hydrocephalus, a condition where cerebrospinal fluid (CSF) collects in the ventricles of the brain of a patient. CSF is produced by the ventricular system and is normally absorbed by the venous system. However, if the CSF is not absorbed, the volume of CSF increases thereby elevating the intracranial pressure. This excess CSF can result in abnormally high epidural and intradural pressures. Left untreated, hydrocephalus can result in serious medical conditions, including subdural hematoma, compression of the brain tissue and impaired blood flow.

Various drainage catheters or shunt systems have been developed to remove excess CSF and thereby reduce the elevated intracranial pressure. Generally, fluid shunt systems include a valve mechanism for controlling or regulating the flow rate of fluid through the system. Shunt systems typically permit fluid flow only when the fluid pressure reaches a threshold pressure for the shunt valve. The threshold pressure should be such that excessive fluid is allowed to drain without creating an undesirable overdrainage condition in which too much fluid is drained from the ventricle. Thus, the shunt system should have a threshold pressure that is balanced to reduce excessive intracranial pressure and avoid overdrainage conditions.

To achieve optimal drainage conditions, it may be desirable to periodically adjust the threshold pressure. For example, a surgeon may initially select a relatively low threshold pressure to trigger fluid flow. Over time, the initial threshold pressure may not be ideal. For example, it could lead to excess fluid flow, creating an undesirable overdrainage condition in which too much fluid is drained from the ventricle. Such a situation may give rise to a need to increase the threshold pressure to afford a fluid flow rate that is balanced to avoid both excessive intracranial pressure and overdrainage conditions.

One prior art shunt valve that allows threshold pressure adjustment without removal of the device is disclosed in U.S. Pat. Nos. 4,615,691 and 4,772,257, both of which are incorporated by reference herein. These patents disclose a cerebrospinal fluid shunt valve that is externally adjustable by means of a programming device. The shunt valve includes a stepping motor having rotor and stator elements. The stator elements are composed of a magnetically soft and permeable material shaped and positioned with respect to the rotor. The external programming device applies a magnetic field causing the rotor to rotate about a central axis so as to adjust the threshold pressure.

After programming the shunt valve and during examinations, the pressure setting of the device should be verified to ensure proper fluid drainage occurs. The pressure setting is generally ascertained using X-ray examination of the device. Known shunt valves and stepping motors generally include radiopaque elements that are observable on a display or other device. From the observed positions of the radiopaque elements, the pressure to which the device has been programmed can be verified. However, X-ray examination can be cumbersome and time consuming. Furthermore, access to X-ray equipment may be limited or the equipment may be unavailable.

It would, therefore, be desirable to provide a system including an apparatus and a device for obtaining information from the implanted apparatus without invasive surgical procedures and/or X-ray examination.

SUMMARY OF THE INVENTION

The present invention provides a shunt system including an implantable apparatus and a device for obtaining pressure information from the apparatus after implantation. Although primarily shown and described as a system for obtaining pressure information from an implanted shunt valve, it is understood that the invention has other applications as well.

In one embodiment, a device for determining the pressure setting of an implanted shunt valve includes a housing having a fluid-filled chamber and a ferromagnetic indicator that is freely movable within the chamber. The housing is adapted to be externally mountable upon the patient's body at a location proximate the implanted shunt valve. A plurality of markings can be affixed on the housing such that each marking corresponds to a specific pressure setting of the shunt valve. The markings can also include a centrally located marking for positioning the device relative to the shunt valve.

To effectively position the ferromagnetic indicator of the device in relation to a pressure setting of the shunt valve, the shunt valve includes an indicator magnet. The indicator magnet generates a magnetic field that biases the ferromagnetic indicator to a particular orientation in relation to the location of the magnetic poles of the indicator magnet. In one embodiment, the indicator magnet is affixed to a cam which forms a portion of a stepping motor for programming the shunt valve to a selected pressure setting. The positions of the cam and the indicator magnet correspond to the pressure setting of the shunt valve.

In operation, after the shunt valve is implanted under the scalp of the patient the device is used to determine the pressure setting of the shunt valve. The housing is mounted on the scalp of a patient over a protrusion corresponding to the implanted shunt valve. The device should be positioned such that the ferromagnetic indicator is aligned with the central marking to ensure that the device is properly positioned in relation to the shunt valve. The position of the ferromagnetic indicator of the device is determined by the relative position of the indicator magnet in the shunt valve which corresponds to the pressure setting of the shunt valve. The pressure setting of the shunt valve is then visually determined based on the orientation of the ferromagnetic indicator with respect to the markings on the housing. More particularly, the ferromagnetic indicator will be generally aligned with one of the markings, each of which indicate a particular pressure setting of the shunt valve.

In another embodiment, a device for determinng pressure setting information from an implanted shunt valve includes a ferromagnetic indicator that is secured to the housing at a pivot point. The ferromagnetic indicator, which is disposed within a chamber formed in the housing, is freely rotatable about the pivot point. A ferromagnetic material is contained in cavities formed in the side walls of the housing. The position of the ferromagnetic material is influenced by an indicator magnet disposed within the shunt valve. Based on the position of the ferromagnetic material, the device can be manipulated to align the ferromagnetic indicator with the indicator magnet in the shunt valve. More particularly, the pivot point of the ferromagnetic indicator should be aligned with the ferromagnetic material in the cavities formed in the side walls of the housing. Once the device is properly positioned, the pressure setting of the shunt valve is determined based on the position of the ferromagnetic indicator with respect to a plurality of markings on the housing, each of which corresponds to a particular pressure setting of the shunt valve.

BRIEF DESCRIPTION OF THE DRAWINGS

The invention will be more fully understood from the following detailed description taken in conjunction with the accompanying drawings, in which.

DETAILED DESCRIPTION OF THE INVENTION

The drawings are understood to be illustrative of the concepts disclosed herein to facilitate comprehension of the invention. Further, the drawings are not to scale, and the scope of the invention is not to be limited by the relative dimensions of various components of the particular embodiments shown and described herein.

Figure 1:
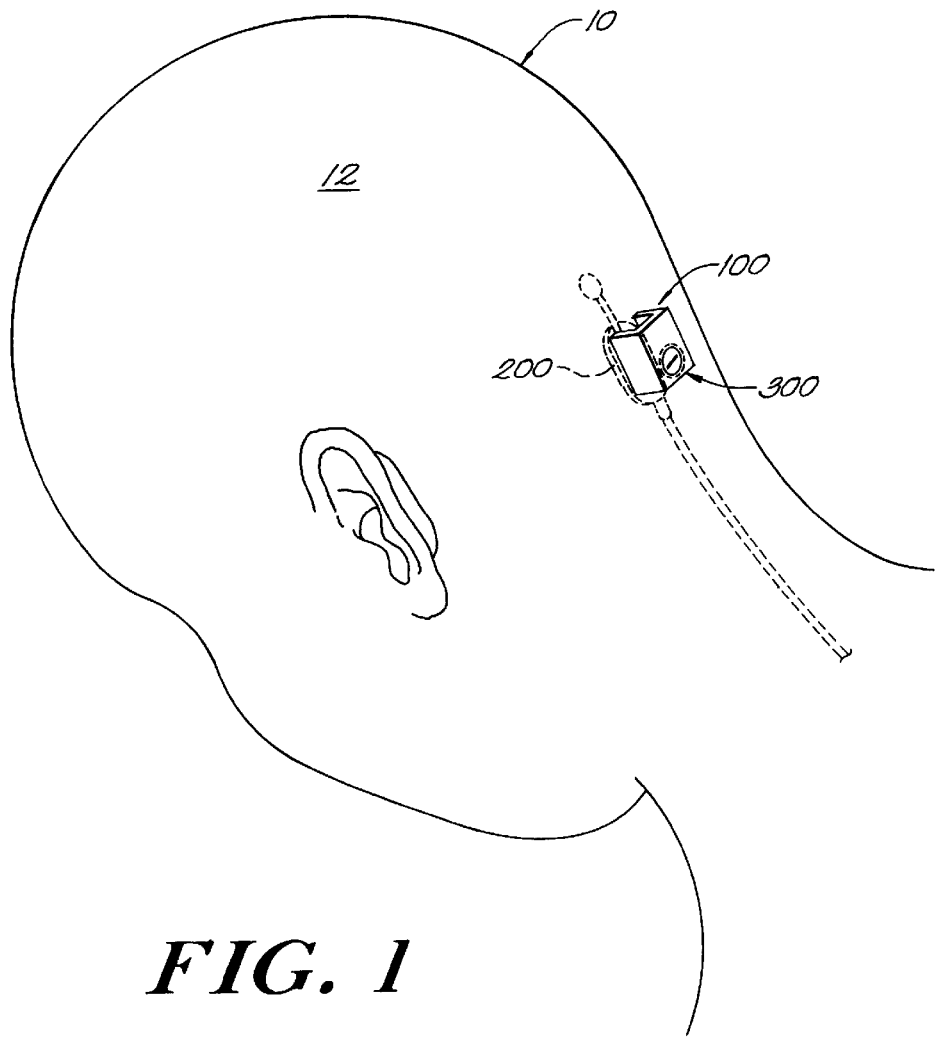
FIG. 1 is a perspective view of an implanted shunt valve and a device for obtaining information from the shunt valve in accordance with the present invention.
Figure 2:
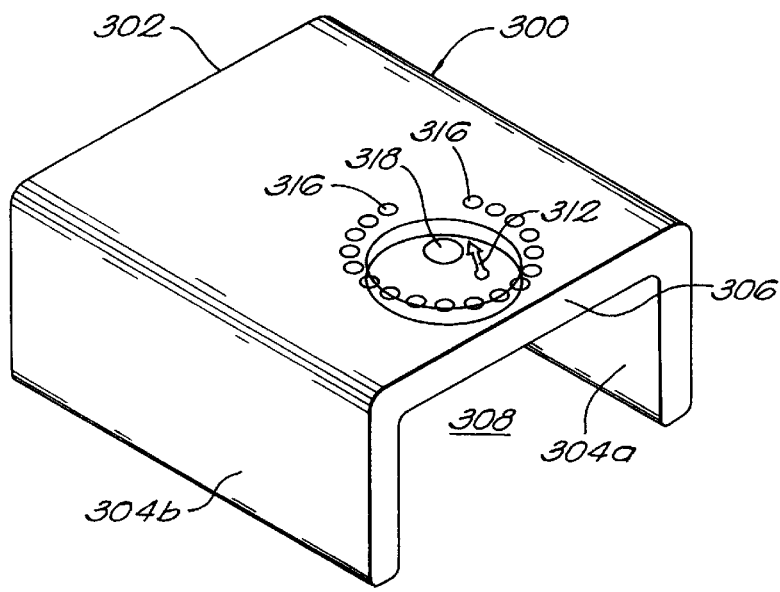
FIG. 2 is a perspective view of the device of FIG. 1.
Figure 3:
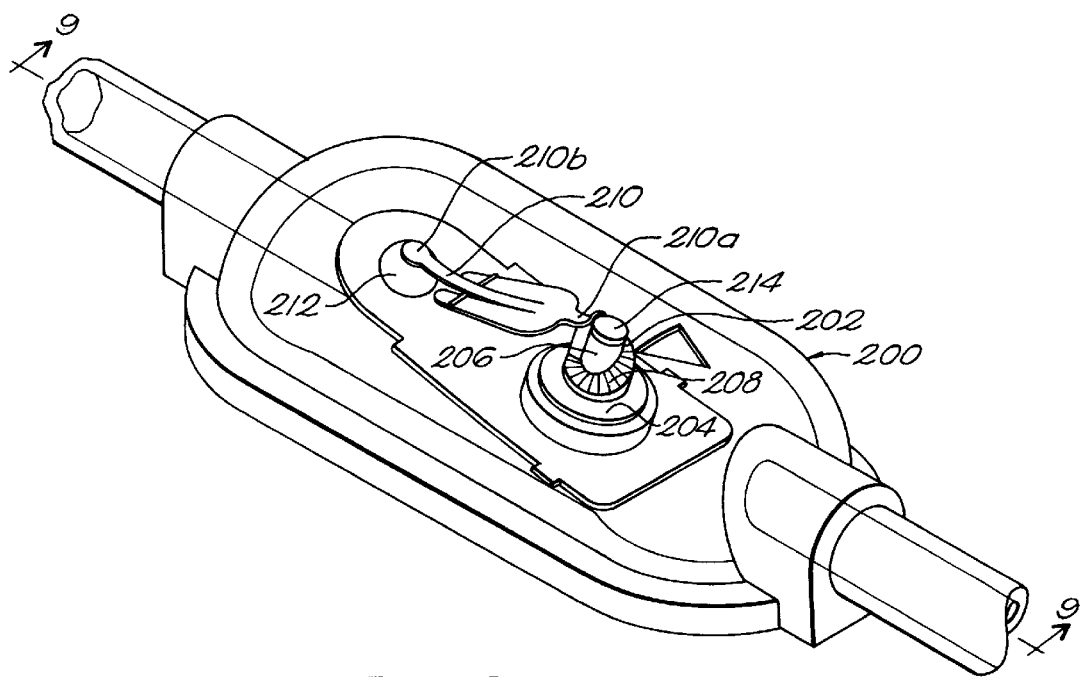
FIG. 3 is a perspective view of the shunt valve of FIG. 1 shown without an exterior portion of the shunt valve.

FIGS. 1–3 show a system 100 including a shunt valve 200 and a device 300 for determining a pressure setting of the shunt valve 200. The shunt valve 200 is implanted under the scalp (not shown) of a patient 10 proximate the skull 12. The device 300 is adapted for being externally mounted on the patient's head over the protrusion corresponding to the implanted shunt valve 200.

Figure 4:
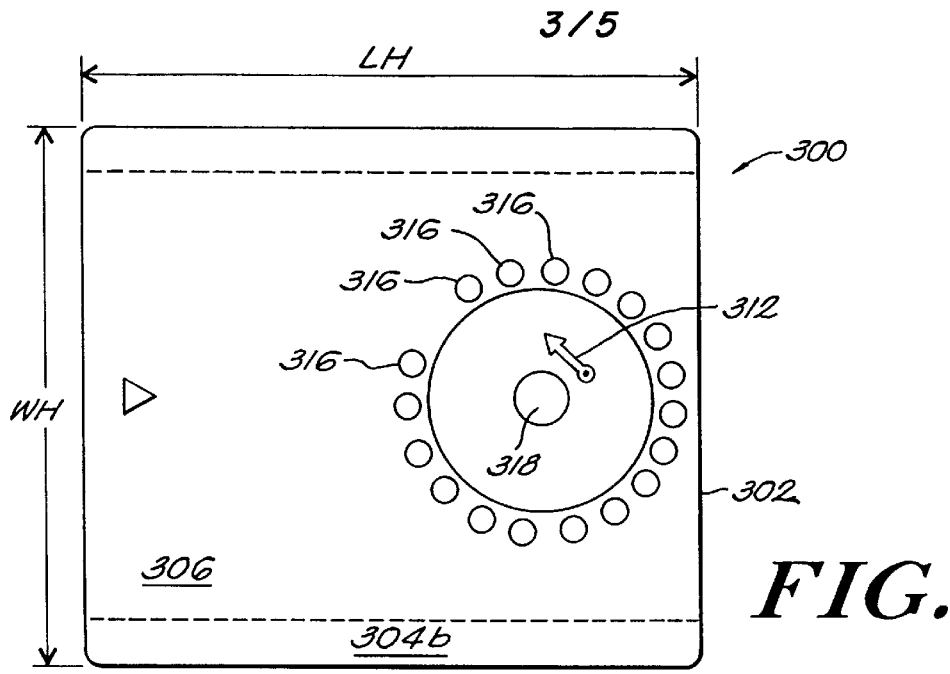
FIG. 4 is a top view of the device of FIG. 1.
Figure 5:
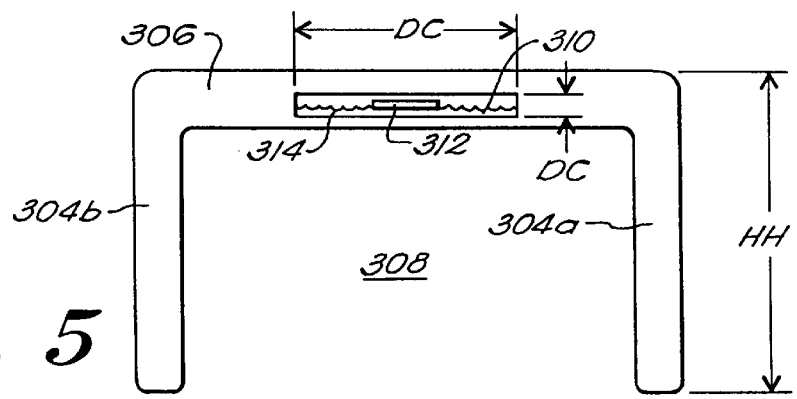
FIG. 5 is a side view of the device of FIG. 1.

As shown in FIGS. 4–5 in conjunction with FIGS. 1–3, the device 300 includes a housing 302 having a geometry adapted for placement against the body of a patient. It is understood that the housing 302 can have a variety of configurations that allow the device 300 to be positioned in relation to an implanted apparatus. In one embodiment adapted for use with the implanted shunt valve 200, the housing 302 includes opposed first and second side walls 304a,b and a top portion 306. The side walls 304 and the top portion 306 together form a channel 308 that is sized to accommodate a protrusion on a patient's scalp corresponding to the implanted shunt valve 200.

Disposed within the top portion 306 of the housing is a chamber 310 (FIG. 5) in which a ferromagnetic indicator 312 is freely movable. The chamber 310 can contain a fluid 314, such as a clear oil, that allows the ferromagnetic indicator 312 to freely move within the chamber 310. The ferromagnetic indicator 312 can float on the fluid 314 or the fluid can facilitate movement of the ferromagnetic indicator by reducing frictional forces.

A plurality of markings 316 indicative of a pressure setting of the implanted apparatus can be affixed on the housing 302. The markings 316 can also include a central marking 318 that can facilitate proper positioning of the device in relation to the implanted shunt valve.

Figure 5A:
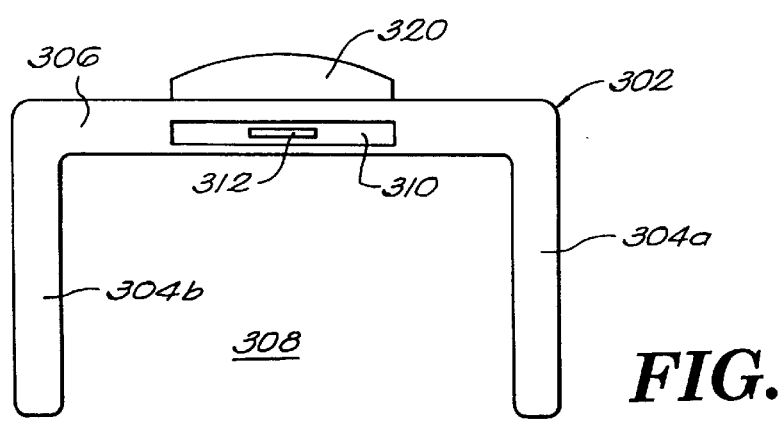
FIG. 5A is a side view of an alternative embodiment of the device of FIG. 1.

As shown in FIG. 5A, the housing 302 can further include a magnifying element 320, such as a lens, that is effective to enhance a visual determination of the position of the relatively small ferromagnetic indicator 312. It is understood that the magnifying element 320 can be affixed to the device or it can be a separate component, such as a loupe type instrument.

Figure 6:
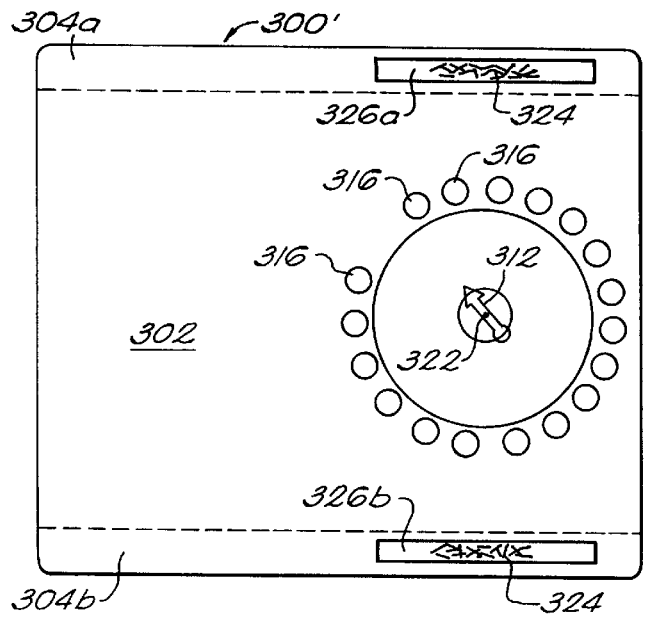
FIG. 6 is a top view of another embodiment of a device in accordance with the present invention.
Figure 7:
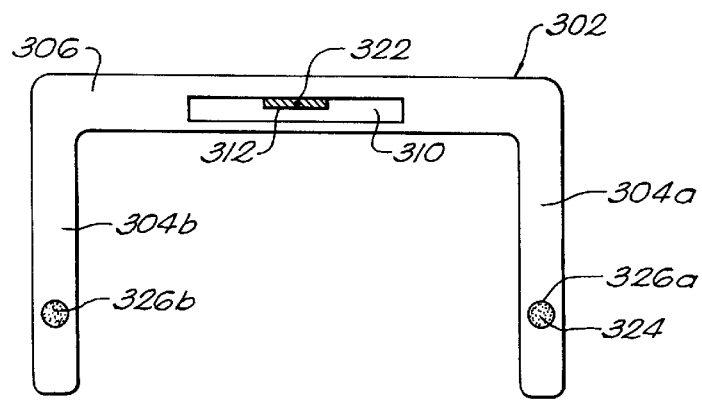
FIG. 7 is a side view of the device of FIG. 6.

FIGS. 6–7 show an alternative embodiment of the device 300' wherein the ferromagnetic indicator 312 is secured to the housing 302 at a pivot point 322. The ferromagnetic indicator 312 is freely rotatable about the pivot point 322. A ferromagnetic material 324, such as iron filings, is contained within first and second cavities 326a,b located in respective first and second wall portions 304a,b of the housing. The ferromagnetic material 324 provides an indication of the relative alignment of the device 300' in relation to the shunt valve 200. That is, when the pivot point 322 is aligned with the ferromagnetic material 324 in the first and second cavities 326a,b, the device 300' is properly positioned in relation to the shunt valve 200. The ferromagnetic indicator 312 then rotates about the pivot point 322 and points to one of the markings 316 on the housing.

Figure 8:
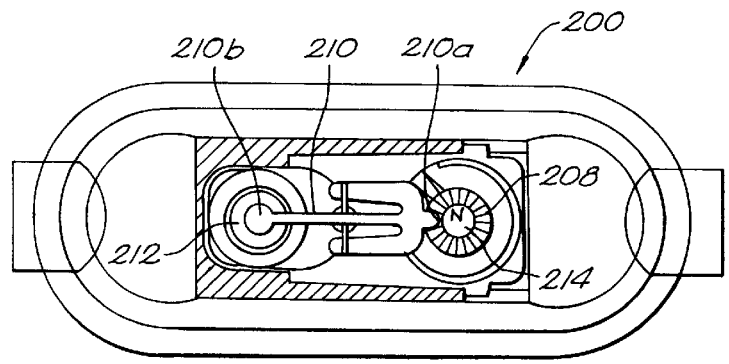
FIG. 8 is a top view of the shunt valve of FIG. 3.
Figure 9:
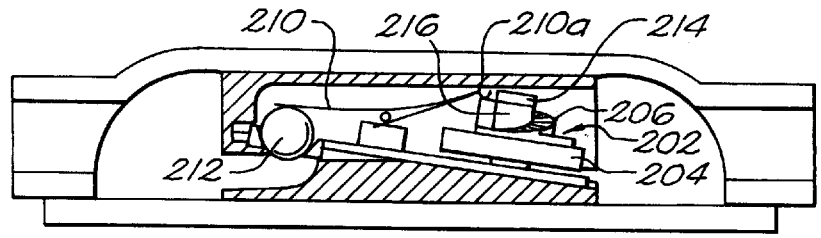
FIG. 9 is a cross-sectional view of the shunt valve of FIG. 3 along lines 9—9.

Referring now to FIGS. 8–9, viewed in conjunction with FIGS. 1–3, the shunt valve 200 is typically implanted under the scalp in fluid communication with a ventricular catheter (not shown) located in the ventricles of the patient's brain. The shunt valve 200 is effective to drain excess cerebrospinal fluid (CSF) to reduce elevated intracranial pressure. The shunt valve 200 includes a stepping motor 202 that is actuable by means of an external programmer (see U.S. Pat. No. 4,772,257) to set a threshold pressure above which CSF flows through the shunt valve. The stepping motor 202 includes a rotor 204 that is effective to rotate a cam 206 having a series of steps 208 formed thereon. The steps 208 sequentially increase in height with respect to the rotor 204. A spring 210 has a first end 210a in contact with the cam 206 and a second end 210b in biased contact with a spherical element 212. The particular step 208 on which the first end 210 of the spring rests determines the pressure applied to the spherical element 212 by the second end 210b of the spring. By rotating the rotor 204 and the cam 206 to position the spring 210 on a particular step 208, one can select a threshold pressure above which CSF will flow through the shunt valve.

The shunt valve 200 includes an indicator magnet 214 to allow the pressure setting of the shunt valve 200, e.g., the position of the cam 206, to be determined by the externally mountable device 300. The indicator magnet 214 is secured within the shunt valve 200 in a fixed position relative to the cam 206 and/or rotor 204. In one embodiment, the indicator magnet 214 is secured to a top portion 216 of the cam such that the indicator magnet is coaxial with both the cam 206 and the rotor 204. The poles of the indicator magnet 214 can be positioned to correspond to a predetermined pressure setting of the shunt valve.

The overall dimensions of the device and shunt valve can vary. In an exemplary embodiment, the device housing 302 has a length LH (FIG. 4) that can range from about 10 millimeters to about 16 millimeters and a width WH that can range from about 8 millimeters to about 24 millimeters. The height HH can vary from about 5 millimeters to about 10 millimeters.

The chamber 310 is generally centered between the sidewalls 304 with a diameter ranging from about 3 millimeters to about 7 millimeters. The depth DC (FIG. 5) of the chamber 310 can vary from about 0.5 millimeter to about 1.5 millimeter and is preferably about 1.0 millimeter.

The ferromagnetic indicator 312 can be formed in a variety of geometries that enhance a visual determination of the position of the indicator. In an exemplary embodiment, the ferromagnetic indicator 312 is elongate or needle-shaped with a length of about 1.3 millimeter.

The indicator magnet 214 housed within the shunt valve 200 is, in an exemplary embodiment, circular with a diameter ranging from about 1.0 millimeter to about 1.2 millimeter with a thickness of about 0.3 millimeter. The indicator magnet 214 generates a magnetic field having a strength in the range from about 100 Gauss to about 500 Gauss.

Figure 10:
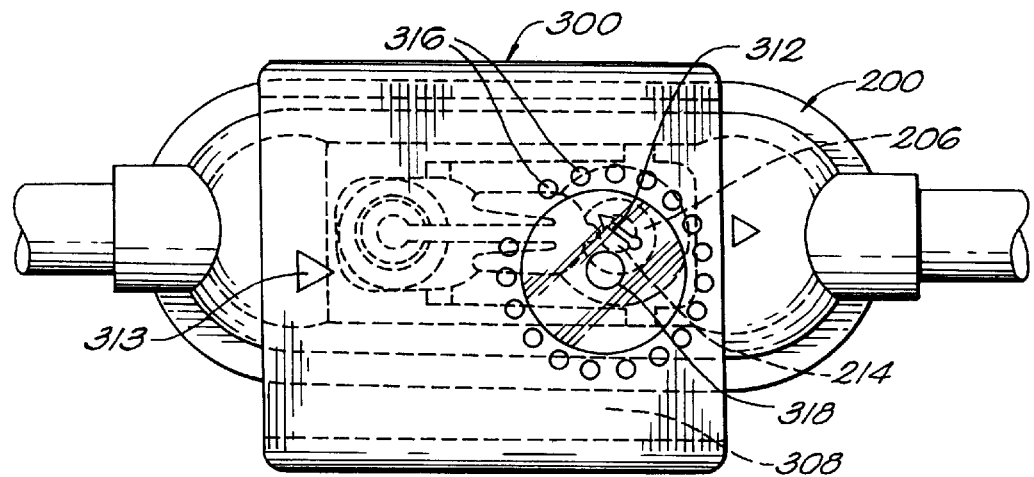
FIG. 10 is a top view of the device and shunt valve of FIG. 1 shown in a first position.
Figure 11:
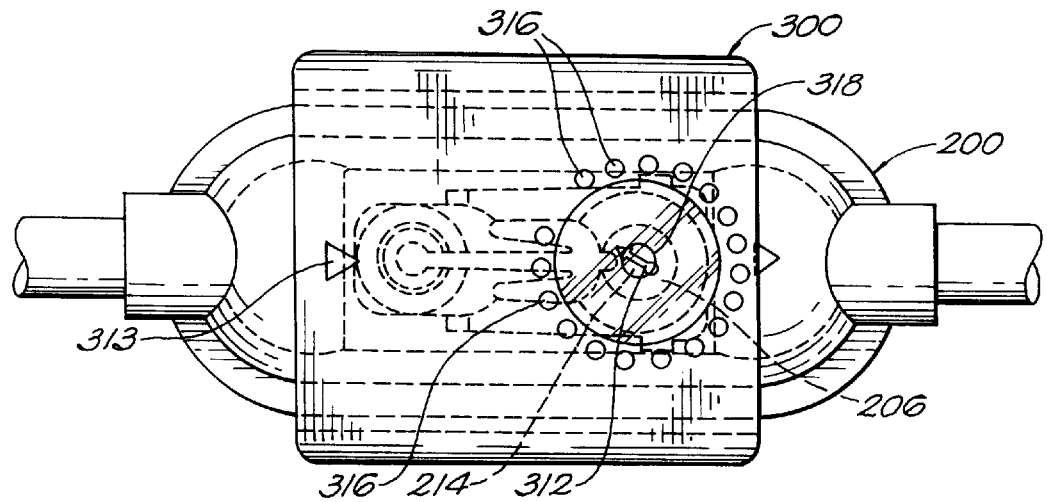
FIG. 11 is a further top view of the device and shunt valve of FIG. 1 shown in a second position.

As shown in FIGS. 10–11, to obtain the pressure setting of the implanted shunt valve 200, the device 300 is mounted upon the patient's scalp such that the protrusion corresponding to the shunt valve is generally within the channel 308 of the housing. An arrow 313 indicates the direction of fluid flow for proper longitudinal orientation of the device. It is understood that CSF flows in a direction from the patient to the shunt valve.

After initial placement on the scalp, the device 300 typically needs to be more accurately positioned with respect to the shunt valve 200. As shown in FIG. 10, for example, after initial placement of the device 300 over the scalp protrusion (not shown) the ferromagnetic indicator 312 is not aligned with the center marking 318. The position of the ferromagnetic indicator 312 is determined by the relative position of the indicator magnet 214 and the cam 206 which correspond to the pressure setting of the shunt valve 200. The device 300 should be manipulated until the ferromagnetic indicator 312 is within the center marking 318 on the housing, as shown in FIG. 11. After the device is properly positioned, the ferromagnetic indicator 312 points to one of the markings 316. Each of these markings corresponds to a particular pressure setting of the shunt valve 200.

It is understood that ferromagnetic, as used herein, refers to a property exhibited by certain metals, alloys, and compounds characterized by an attraction to a magnetized body. The ferromagnetic indicator, for example, may be comprised of a ferrite steel in one embodiment. Alternatively, the ferromagnetic indicator can be a composite material containing ferromagnetic and non-ferromagnetic materials.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A device for obtaining parameter setting information from a surgically implantable apparatus that includes a stepping motor having a rotor for rotating a cam with an indicator magnet in a fixed position in relation to the cam, the device comprising:

an externally mountable housing having a chamber and a contact surface adapted to be mountable on the patient's body proximate the apparatus; and a ferromagnetic indicator disposed and freely movable within the chamber such that a position of the ferromagnetic indicator corresponds to a position of the indicator magnet which is indicative of a position of the cam and the pressure setting of the apparatus.

2. The device according to claim 1, wherein the apparatus is an externally programmable shunt valve implantable beneath the patient's scalp.

3. The device according to claim 1, wherein the housing includes first and second side walls and a top portion, that together define a channel that is sized to accommodate a protrusion on a patient's scalp corresponding to the implanted apparatus.

4. The device according to claim 1, wherein the ferromagnetic indicator is rotatably affixed to the housing at a pivot point.

5. The device according to claim 1, further including a magnifying element disposed on the housing, the magnifying element being effective to enhance a visual determination of a position of the ferromagnetic indicator.

6. A device for obtaining parameter setting information from a surgically implantable apparatus that includes a stepping motor having a rotor for rotating a cam with an indicator magnet in a fixed position in relation to the cam, the device comprising:

an externally mountable housing having a chamber with a fluid disposed therein and a contact surface adapted to be mountable on the patient's body proximate the apparatus; and a ferromagnetic indicator disposed within the chamber such that a position of the ferromagnetic indicator corresponds to a position of the indicator magnet which is indicative of a position of the cam and the pressure setting of the apparatus.

7. A device for obtaining parameter setting information from a surgically implantable apparatus that includes a stepping motor having a rotor for rotating a cam with an indicator magnet in a fixed position in relation to the cam, the device comprising:

an externally mountable housing having a chamber and a contact surface adapted to be mountable on the patient's body proximate the apparatus; and a ferromagnetic indicator disposed within the chamber such that a position of the ferromagnetic indicator corresponds to a position of the indicator magnet which is indicative of a position of the cam and the pressure setting of the apparatus; and a plurality of markings affixed to the housing, each marking corresponding to a specific pressure setting of the apparatus, wherein the markings include a central marking for aligning the ferromagnetic indicator with the indicator magnet.

8. A device for obtaining parameter setting information from a surgically implantable apparatus that includes a stepping motor having a rotor for rotating a cam with an indicator magnet in a fixed position in relation to the cam, the device comprising:

an externally mountable housing having a chamber and a contact surface adapted to be mountable on the patient's body proximate the apparatus; and a ferromagnetic indicator disposed within the chamber and rotatably affixed to the housing at a pivot point such that a position of the ferromagnetic indicator corresponds to a position of the indicator magnet which is indicative of a position of the cam and the pressure setting of the apparatus; and a ferromagnetic material disposed within the housing that is effective to align the ferromagnetic indicator with the indicator magnet.

9. An implantable shunt valve effective to provide pressure setting information to an externally positioned device, the shunt valve comprising:

a stepping motor having a rotor for rotating a cam, wherein a position of the cam corresponds to a pressure setting of the shunt valve; and an indicator magnet in a generally fixed position with respect to the cam, wherein the indicator magnet generates a magnetic field having a strength in the range from about 100 gauss to about 500 gauss, wherein the position of the indicator magnet is effective to influence a position of a ferromagnetic indicator that forms part of the externally positioned device such that the position of the ferromagnetic indicator corresponds to the pressure setting of the shunt valve.

10. The shunt valve according to claim 9, wherein the indicator magnet has a magnetic pole orientation corresponding to a predetermined pressure setting of the shunt valve.

11. A shunt valve system, comprising:

an implantable shunt valve including a stepping motor having a rotor and a cam, wherein a position of the cam corresponds to a pressure setting of the shunt valve; and an indicator magnet secured to and substantially coaxial with the rotor; and an externally mountable device for determining the pressure setting of the shunt valve when it is implanted beneath a patient's scalp, the externally mountable device including a housing defining a chamber and a contact surface adapted to be mountable on the patient's scalp proximate the shunt valve; and a ferromagnetic indicator freely movable and disposed within the chamber such that a position of the ferromagnetic indicator corresponds to a position of the indicator magnet which is indicative of the cam position and the pressure setting of the shunt valve.

12. The system according to claim 11, wherein the indicator magnet is substantially coaxial with the cam.

13. The system according to claim 11, further including a plurality of markings located on the housing wherein each of the plurality of markings corresponds to a predetermined pressure setting of the shunt valve.

* * * * *